United States Patent [19]

Schwieker

[11] Patent Number: 5,581,830
[45] Date of Patent: Dec. 10, 1996

[54] UROLOGICAL EXAMINATION APPARATUS

[75] Inventor: Horst Schwieker, Hamburg, Germany

[73] Assignee: U.S. Philips Corporation, New York, N.Y.

[21] Appl. No.: 247,723

[22] Filed: May 23, 1994

[30] Foreign Application Priority Data

May 21, 1993 [DE] Germany ............... 43 16 961.9

[51] Int. Cl.⁶ ..................... A61G 13/00; A61G 7/04
[52] U.S. Cl. ................... 5/606; 5/928; 604/356; 604/357
[58] Field of Search .............. 5/606, 928; 4/638; 604/356, 357

[56] References Cited

U.S. PATENT DOCUMENTS

| | | | |
|---|---|---|---|
| 3,386,444 | 6/1968 | Brenner et al. | 5/606 X |
| 4,007,741 | 2/1977 | Waldrop et al. | 604/357 |
| 4,221,371 | 9/1980 | Kuphal | 5/606 |
| 4,880,418 | 11/1989 | Tramont | 604/356 |
| 5,263,076 | 11/1993 | Elff et al. | 378/162 |

FOREIGN PATENT DOCUMENTS 4112148  10/1992  Germany.

Primary Examiner—Michael F. Trettel
Attorney, Agent, or Firm—Jack Slobod

[57] ABSTRACT

A urological examination apparatus, includes a patient table at the foot of which there is provided a sink which serves to collect fluids and which is provided with a drain. The sink is pivotable about a horizontal shaft which extends perpendicularly to the longitudinal direction of the table.

3 Claims, 2 Drawing Sheets

UROLOGICAL EXAMINATION APPARATUS

BACKGROUND OF THE INVENTION

1. Field of the Invention

The invention relates to a urological examination apparatus which comprises a patient table, at the foot end of which there is provided a sink which serves to collect fluids and which is provided with a drain.

2. Description of the Related Art

During a series of urological examinations bodily fluids or rinsing fluids are released, which fluids are to be collected and drained by the sink. Such a sink should not interfere with the examiner during the examination and with the access to the urological examination apparatus. They cannot be moved underneath the examination table, because they then interfere with examinations performed in conjunction with X-ray fluoroscopy, they must also be environmentally acceptable. The systems of sinks used for this purpose in practice satisfy these requirements only conditionally.

Sinks are known which can be displaced laterally or which can be lowered. The lateral access to the apparatus is thus impeded or the leg space for the examiner is limited; moreover, the sinks cannot perform their function in these positions. Also known are collapsible receptacle systems which are used only once. On the one hand, these systems are not sufficiently stable and on the other hand they represent a burden to the environment.

SUMMARY OF THE INVENTION

It is an object of the present invention to provide a urological examination apparatus which better satisfies the described requirements.

This object is achieved in accordance with the invention in that the sink is pivotable about a horizontal shape which extends perpendicularly to the longitudinal direction of the table.

In accordance with the invention, the sink can be pivoted downwards to a position in which it can still collect fluid however, without obstructing the examiner.

In a preferred embodiment of the invention, the distance between the drain and the edge of the sink which is remote from the shape is smaller than the distance between the drain and the shape. By using this shape of the sink it is achieved that the fluid flowing into the sink reaches the drain also when the sink has been pivoted downwards to the position in which it obstructs the examiner the least.

In a further embodiment of the invention, the sink forms part of a unit connected to the patient table. The unit can be completely removed for examinations or treatments where no fluid is to be collected, for example during lithotripsy.

BRIEF DESCRIPTION OF THE DRAWING

The invention will be described in detail hereinafter with reference to the drawings. Therein.

DETAILED DESCRIPTION OF THE PREFERRED EMBODIMENTS

Figure 1:
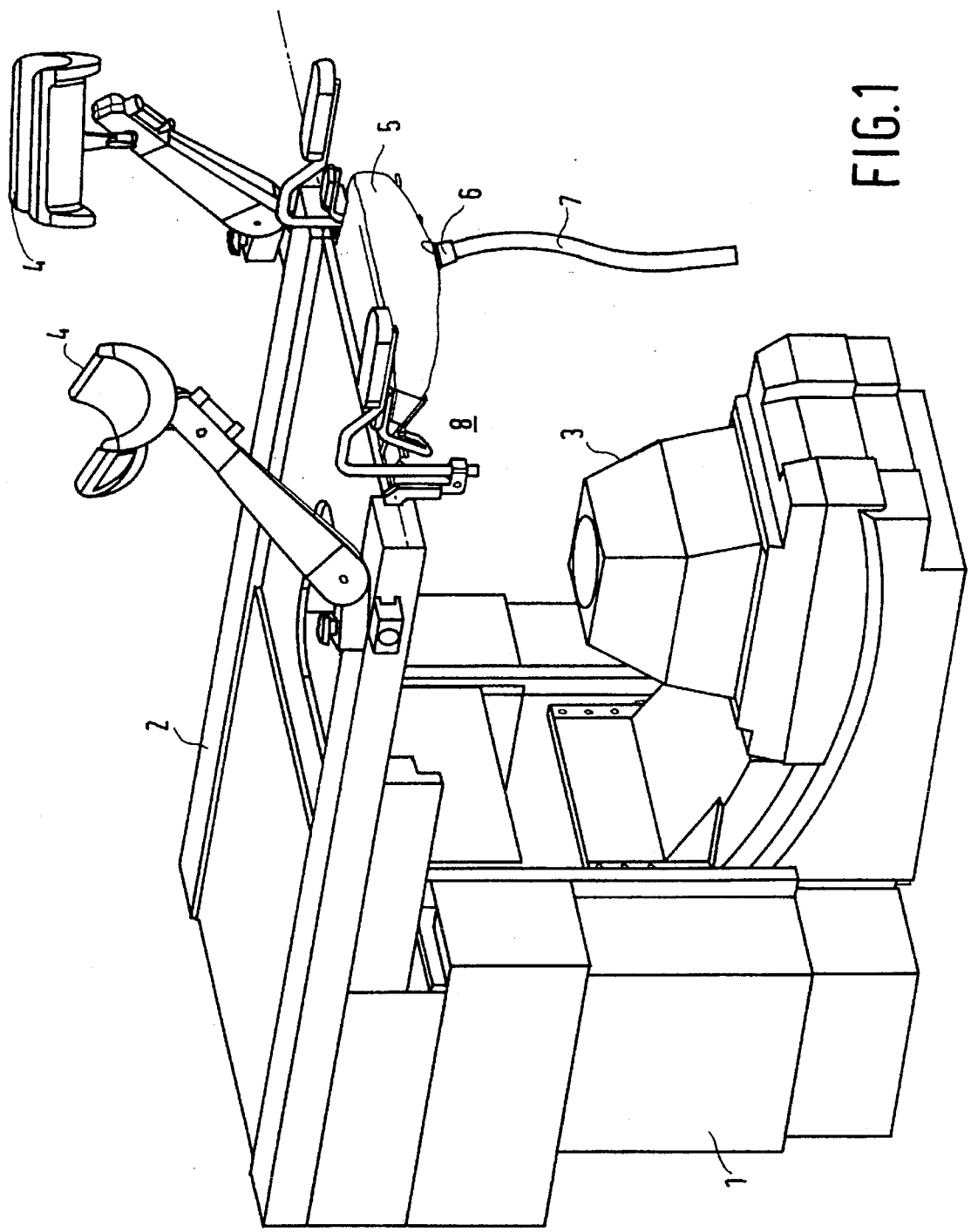
FIG. 1 is a perspective view of a urological apparatus in accordance with the invention.

The urological examination apparatus shown in FIG. 1 comprises a patient table 1 with a horizontally arranged table top 2. Underneath the table top 2 there is arranged an X-ray source 3 which is displaceable along a curved path. As is described in DE-OS 41 12 148 which corresponds to U.S. Pat. No. 5,263,076, above the table top 2 there is arranged an X-ray image intensifier (not shown) for forming X-ray (fluoroscopic) images. At the foot of the table top 2 there are provided leg rests 4 for the patient as well as a sink 5 for collecting fluids. The sink 5 comprises a drain 6 whereto a tube 7 is connected for discharging the fluid collected in the sink 5.

Figure 2:
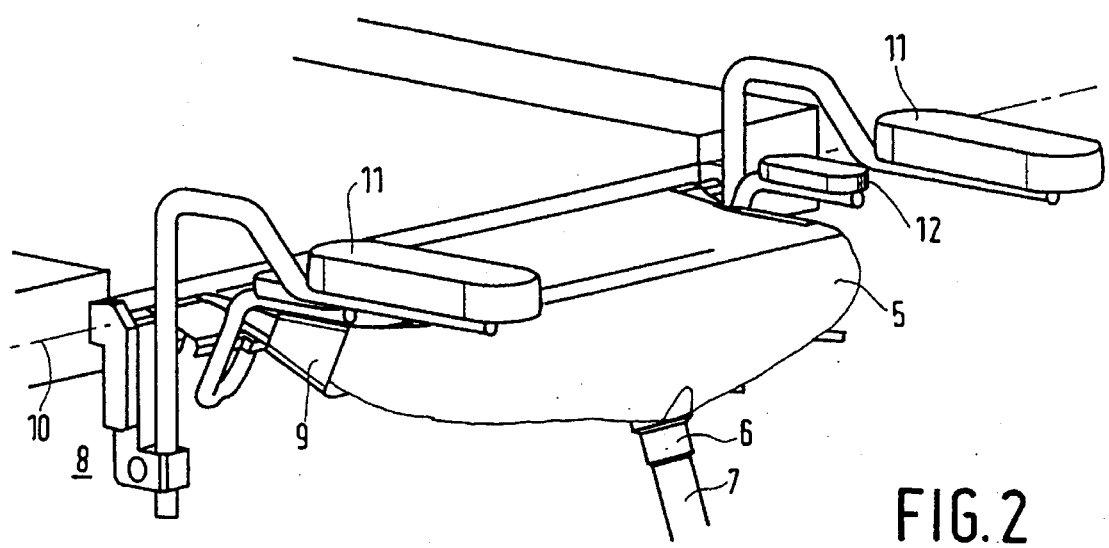
FIG. 2 shows the sink of this apparatus at an increased scale.

As appears from FIG. 2, the sink 5 forms part of a unit 8 which can be coupled, as one unit, to the foot of the patient table. The unit 8 comprises a holder 9 in which the sink, preferably made of a synthetic material, can be inserted, its end at the side of the foot engaging around a shaft 10 about which the holder 9, and hence the sink 5, is pivotable. The shaft extends horizontally and perpendicularly to the longitudinal direction of the table top 2. To the side of the sink the unit 8 also comprises elbow rests 11 for the examiner as well as grips 12 for pivoting the sink 5 downwards.

Figure 3:
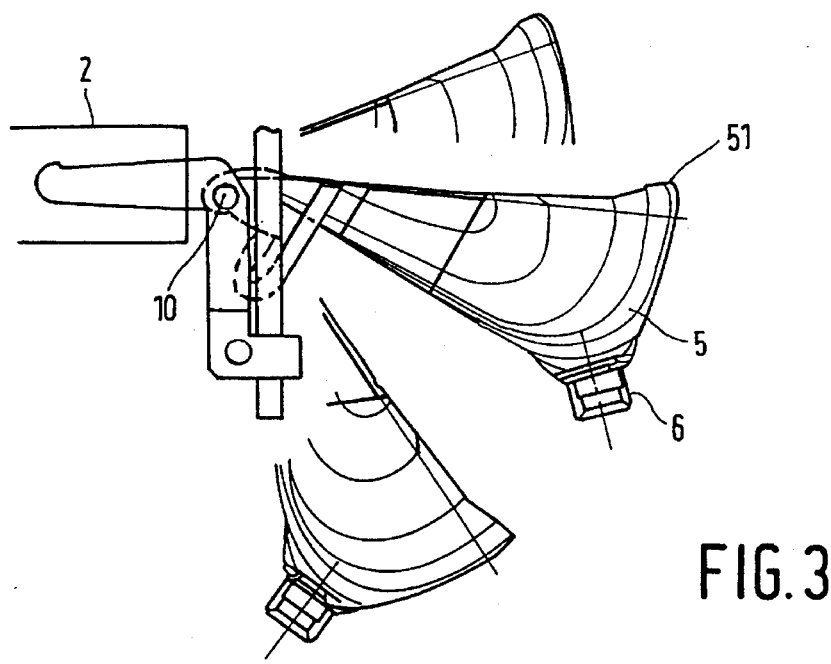
FIG. 3 shows the sink in various positions.

FIG. 3 is a side elevation of the sink 5 in various pivotal positions. It appears that the sink is constructed so that the distance between the drain 6 and the upper edge of the sink which is remote from the shaft 10 is substantially smaller than its distance from the shaft 10. This enables the sink to be pivoted downwards from the central position through an angle of approximately 60°, it nevertheless still being possible to discharge the fluid collected by the sink via the drain 6. In this position of the sink the examiner will hardly be obstructed by the sink, for example during urotroscopy, and in this position the sink does not interfere either with a simultaneously performed X-ray fluoroscopy. The sink can be pivoted to the upper position shown, for example when an endoscope introduced into a body orifice during, for example a urological examination is to be withdrawn and subsequently the jet of fluid emanating is to be collected.

Figure 4:
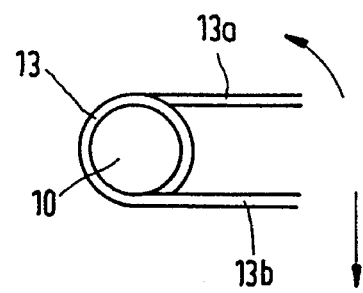
FIG. 4 shows the spring system keeping the sink in different pivotal positions.

A spring system is provided to enable the sink to be moved steplessly to any intermediate position between the upper and the lower position and to keep the sink in this position. The spring system is formed by a loop spring 13 which is diagrammatically shown in FIG. 4 and which is looped around the shaft 10. This loop spring is very rigid and comprises two sections 13a and 13b which are spaced a few spring turns apart. When a downwards directed force is exerted on the upper section 13a, or an upwards directed force is exerted on the lower section 13b, the spring does not change its position relative to the shaft 10, because the spring is firmly looped around the shaft. However, when an upwards directed force is exerted on the section 13a or a downwards directed force acts on the section 13b, the looping around the shaft 10 by the spring 13 relaxes, so that the spring is moved upwards or downwards, respectively. The holder 9 is connected to the section 13a, whereas the grip 12 is connected to the section 13b. Therefore, the examiner can move the sink downwards by way of the grip 12 and can move the sink 5 upwards, by pressing by way of a knee or an arm, to a position in which the sink remains as soon as the pressure exerted on the grip 12 or the sink 5 decreases.

I claim:

1. A urological examination apparatus which comprises a patient table (1, 2) at the foot of which there is provided a sink (5) which serves to collect fluids and which is provided with a drain (6), characterized in that the sink (5) is pivotable about a horizontal shaft (10) which extends perpendicularly to the longitudinal direction of the table, and wherein the sink (5) is controlled by means of a spring system (13) so that it is retained in any pivotal position within a predetermined angular range.

2. A urological examination apparatus as claimed in claim 1, characterized in that the distance between the drain (6) and the edge (51) of the sink (5) which is remote from the shaft is smaller than the distance between the drain (6) and the shaft (10).

3. A urological examination apparatus as claimed in claim 1, characterized in that the sink (5) forms part of a unit (8) which is detachably connected to the patient table.

* * * * *